(12) United States Patent
Naito

(10) Patent No.: US 8,187,170 B2
(45) Date of Patent: May 29, 2012

(54) OVERTUBE AND ENDOSCOPE SYSTEM SUITABLE FOR TREATMENT SUCH AS SUBMUCOSAL DISSECTION

(75) Inventor: Kimihiko Naito, Musashino (JP)

(73) Assignee: Olympus Medical Systems Corp., Tokyo (JP)

( * ) Notice: Subject to any disclaimer, the term of this patent is extended or adjusted under 35 U.S.C. 154(b) by 322 days.

(21) Appl. No.: 12/432,106

(22) Filed: Apr. 29, 2009

(65) Prior Publication Data

US 2009/0275798 A1  Nov. 5, 2009

(30) Foreign Application Priority Data

May 1, 2008 (JP) ................... 2008-119893

(51) Int. Cl.
*A61B 1/00* (2006.01)
(52) U.S. Cl. .............. 600/106; 600/104; 600/114
(58) Field of Classification Search .......... 600/104, 600/106, 114; 604/528
See application file for complete search history.

(56) References Cited

U.S. PATENT DOCUMENTS

| | | | | |
|---|---|---|---|---|
| 616,672 | A * | 12/1898 | Kelling | 600/142 |
| 5,448,989 | A * | 9/1995 | Heckele | 600/142 |
| 7,241,263 | B2 * | 7/2007 | Boulais | 600/137 |
| 7,637,905 | B2 * | 12/2009 | Saadat et al. | 606/1 |
| 7,785,333 | B2 * | 8/2010 | Miyamoto et al. | 606/144 |
| 2002/0183591 | A1 * | 12/2002 | Matsuura et al. | 600/127 |
| 2004/0019254 | A1 * | 1/2004 | Belson et al. | 600/146 |
| 2004/0059322 | A1 | 3/2004 | Kawai et al. | |
| 2005/0222495 | A1 * | 10/2005 | Okada et al. | 600/114 |
| 2008/0051629 | A1 * | 2/2008 | Sugiyama et al. | 600/114 |
| 2008/0287961 | A1 * | 11/2008 | Miyamoto et al. | 606/127 |
| 2009/0326319 | A1 * | 12/2009 | Takahashi et al. | 600/106 |
| 2010/0160728 | A1 * | 6/2010 | Yoshie | 600/109 |

FOREIGN PATENT DOCUMENTS

| | | |
|---|---|---|
| EP | 2 052 671 A2 | 4/2009 |
| JP | 08-224244 | 9/1996 |
| JP | 2004-089591 | 3/2004 |
| JP | 2004-154877 | 6/2004 |
| WO | 2007/146987 A2 | 12/2007 |

* cited by examiner

*Primary Examiner* — John P Leubecker
*Assistant Examiner* — Arnaldo Torres Diaz
(74) *Attorney, Agent, or Firm* — Scully, Scott, Murphy & Presser, P.C.

(57) ABSTRACT

An overtube includes: an endoscope insertion portion passing hole through which an insertion portion of an endoscope is passed; and at least one manipulator passing hole through which a manipulator insertion portion of a manipulator apparatus is passed. The manipulator insertion portion includes a driving portion which has at least one first joint and one second joint rotating clockwise and counterclockwise. The endoscope insertion portion passing hole includes an endoscope protrusion amount determination portion which determines a length of a protrusion of the endoscope; and an observation optical system observation direction determination portion which determines an observation direction of the endoscope. The manipulator passing hole includes a manipulator protrusion amount determination portion which determines positions of the first joint of the manipulator within the observation optical system; and a joint driving direction determination portion which determines rotating directions of shafts of joints within the observation direction.

14 Claims, 9 Drawing Sheets

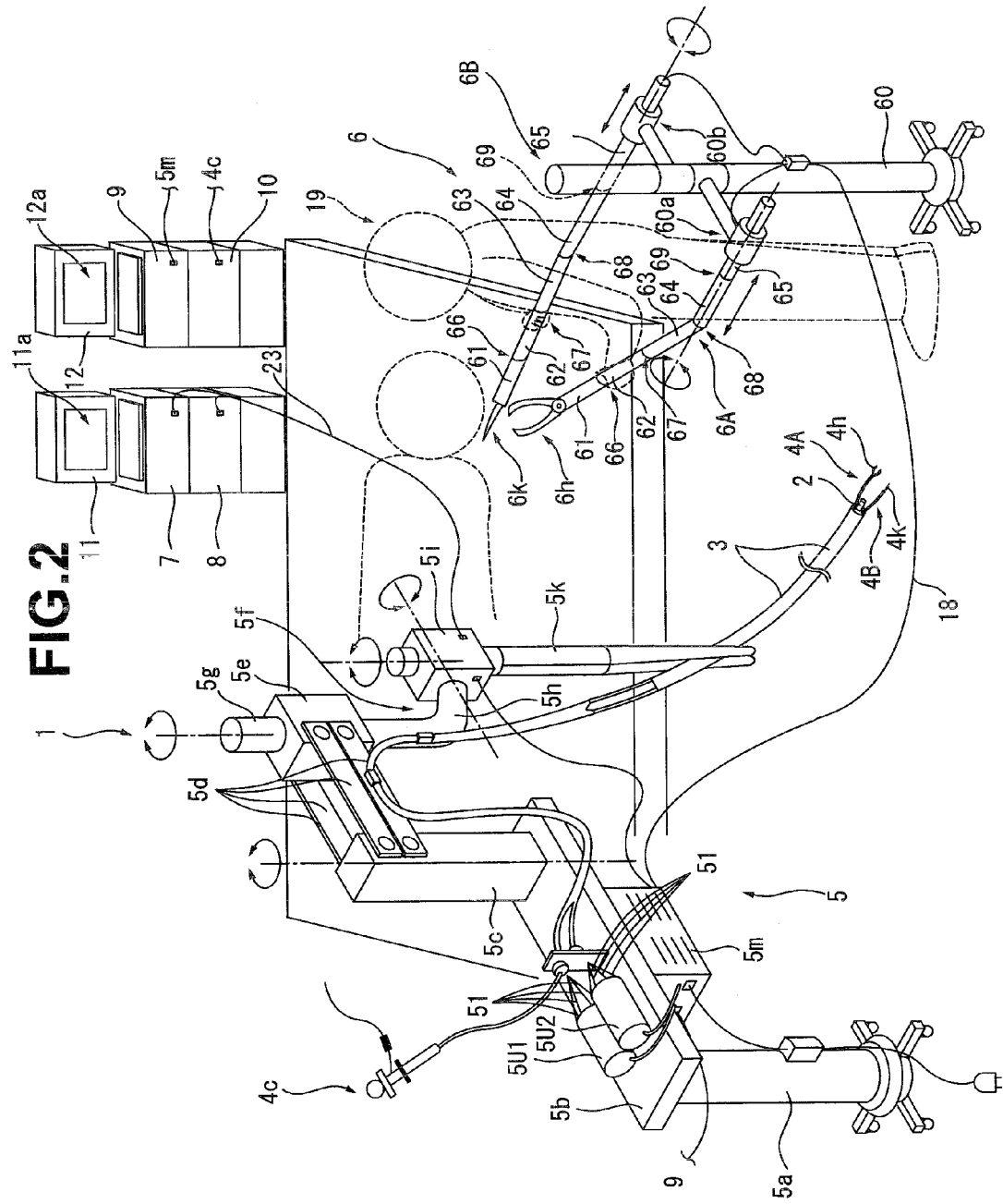

FIG.15
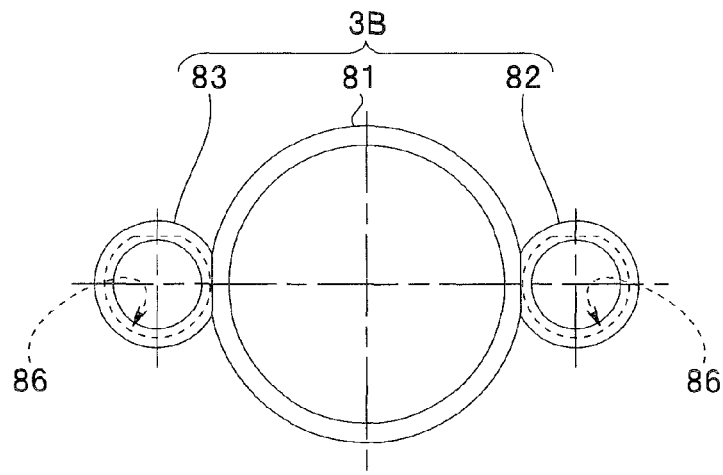
FIG.16
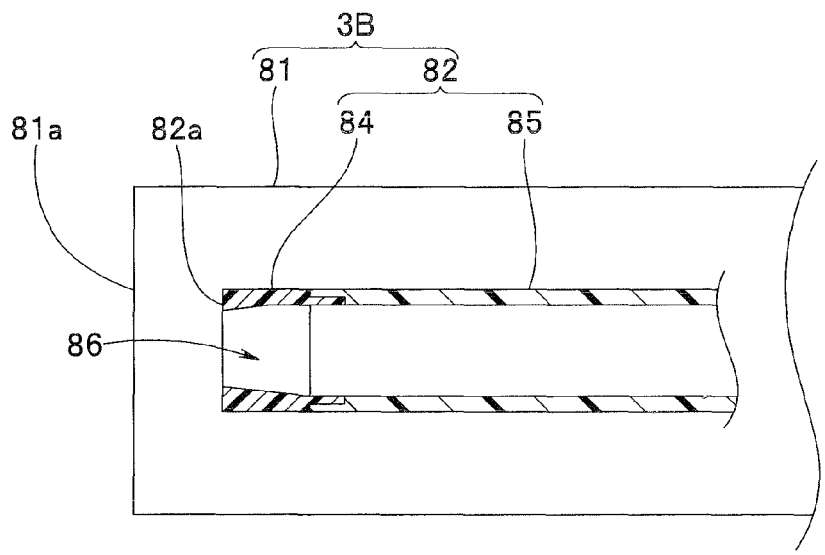
FIG.17A          FIG.17B
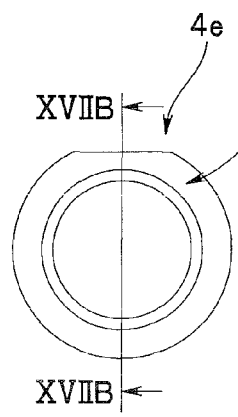   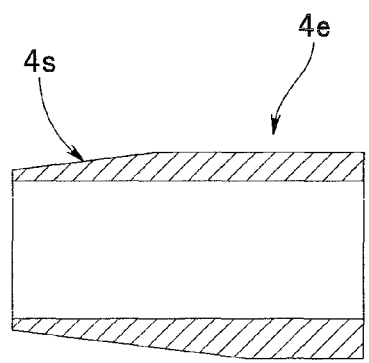

OVERTUBE AND ENDOSCOPE SYSTEM SUITABLE FOR TREATMENT SUCH AS SUBMUCOSAL DISSECTION

This Application claims benefit of Japanese Application No. 2008-119893 filed in Japan on May 1, 2008, the contents of which are incorporated by this reference.

BACKGROUND OF THE INVENTION

1. Field of the Invention

The present invention relates to an overtube and an endoscope system for performing treatment such as submucosal dissection using a manipulator apparatus under observation by an endoscope.

2. Description of the Related Art

In recent years, procedures have been performed such as endoscopic mucosal resection (EMR) or endoscopic submucosal dissection (ESD) of providing a plurality of treatment instrument channels in an insertion portion of an endoscope, introducing treatment instruments such as a grasping device and an IT knife into a body through the respective treatment instrument channels to resect a lesion in mucosal tissue in the body. Clinicians who preform the procedures need good skills.

In recent years, various manipulators including an active joint have been invented for a treatment instrument to be inserted into a treatment instrument channel of an endoscope to improve operability of an operator.

For example, Japanese Patent Application Laid-Open Publication No. 2004-89591 (hereinafter referred to as Document 1) discloses a medical manipulator system including a plurality of manipulators. The medical manipulator system includes the plurality of manipulators having treatment tools in distal ends. In the medical manipulator system, single joint manipulators 11, 12 and 13 each including one joint protrude from holes provided in an insertion cylinder 15 as shown in FIG. 2 in Document 1. The manipulator is not limited to the single joint manipulator, but may be a multijoint manipulator (also referred to as a multi-degree-of-freedom manipulator) including a plurality of joints.

An example of the multijoint manipulator is a multijoint knife 100 in FIG. 1. The knife 100 includes, for example, a prismatic drive joint 102, a pitch drive joint 103, a yaw drive joint 104, a pitch drive joint 103, and a yaw drive joint 104 in order as active joints on a distal end side of a treatment instrument insertion portion 101, and includes a knife arm 105 on a distal end side of the yaw drive joint 104 at a most distal end.

FIGS. 4(*a*) and (*b*) in Japanese Patent Application Laid-Open Publication No. 2004-154877 (hereinafter referred to as Document 2) show a multijoint manipulator including consecutive yaw drive joints and consecutive pitch drive joints. Further, FIG. 3 in Japanese Patent Application Laid-Open Publication No. 8-224244 (hereinafter referred to as Document 3) shows a multijoint manipulator including a plurality of rotary joints only as pitch drive joints.

The multijoint manipulator is operated by solving an inverse problem or a forward problem. An operation by solving a forward problem is an operation in a so-called master/slave mode, and an operator operates a master portion and thus a slave portion reproduces movement of the master portion.

On the other hand, in an operation by solving an inverse problem, an operator provides target values of a position and an attitude of a distal end of, for example, a knife arm. Then, a CPU solves a joint angle path of each joint for the target values, then operates a drive actuator (not shown), pulls and releases an operation wire (not shown) by a predetermined amount to rotate each joint clockwise or counterclockwise to change a joint angle. Then, the position and the attitude of the distal end of the knife arm are set to the target values.

In the case of solving the inverse problem and setting the position and the attitude of the distal end of the knife arm to the target values in a body as described above, the operator needs to previously grasp a situation around the knife arm. If the operator insufficiently grasps the situation, an operation of the active joint may bring the knife arm or the joint into contact with a body wall or the like. In the master/slave mode, for example, the operator operates a master portion to move the knife arm or the like while observing an endoscope image. Thus, the operation of the knife arm can be stopped by the operator stopping the operation of the master portion, thereby preventing the disadvantage described above.

However, in Document 1, when the plurality of multijoint manipulators are protruded from the holes in the insertion cylinder 15 to perform treatment, a distance between an endoscope 10 provided in the hole in the insertion cylinder 15 and an area to be treated increases with increasing number of joints of the manipulators. This reduces a size ratio of an image of the area to be treated displayed on a screen of a display apparatus with respect to a size of the screen. To eliminate the disadvantage, if the endoscope 10 is protruded from the hole in the insertion cylinder 15 and brought close to an observation area, joints or the like on a proximal end side of a distal end surface of the endoscope are not displayed on the screen.

SUMMARY OF THE INVENTION

An overtube of the present invention includes: an endoscope insertion portion passing hole, through which an endoscope insertion portion of an endoscope including an observation optical system in a distal end portion of the endoscope insertion portion is passed, having an endoscope protrusion amount determination portion which determines a length of a distal end portion of the endoscope insertion portion protruding from a distal end surface of the overtube, and an observation optical system observation direction determination portion which determines vertical and lateral observation directions of the observation optical system portion, and at least one manipulator passing hole, through which a manipulator insertion portion of a manipulator apparatus is passed, the manipulator apparatus including a driving portion with a plurality of joint pieces connected on a distal end side of the manipulator insertion portion, adjacent joint pieces among the plurality of joint pieces being connected by connecting shafts, and configured as a first joint rotating clockwise and counterclockwise around a first shaft and a second joint rotating clockwise and counterclockwise around a second shaft perpendicular to the first shaft, at least one first joint and at least one second joint being provided in order from the distal end side, having a manipulator protrusion amount determination portion which determines a protrusion amount from the distal end surface of the overtube so that the first joint of the driving portion provided in the manipulator insertion portion is placed within an observation range of the observation optical system, and a joint driving direction determination portion which determines the first shaft of the first joint and the second shaft of the second joint of the driving portion provided in the manipulator insertion portion in an observation direction of the observation optical system.

An endoscope system includes: an endoscope; a manipulator apparatus; and an overtube. The endoscope includes an observation optical system in a distal end portion of an endoscope insertion portion. The manipulator apparatus includes a driving portion with a plurality of joint pieces connected on a distal end side of a manipulator insertion portion. Adjacent joint pieces among the plurality of joint pieces are connected by connecting shafts, and configured as a first joint rotating clockwise and counterclockwise around a first shaft and a second joint rotating clockwise and counterclockwise around a second shaft perpendicular to the first shaft, and at least one first joint and at least one second joint are provided in order from the distal end side. The overtube includes an endoscope insertion portion passing hole through which the endoscope insertion portion of the endoscope is passed, and at least one manipulator passing hole through which the manipulator insertion portion of the manipulator apparatus is passed. The endoscope insertion portion passing hole includes an endoscope protrusion amount determination portion and an observation optical system observation direction determination portion. The manipulator passing hole includes a manipulator protrusion amount determination portion and a joint driving direction determination portion. The endoscope protrusion amount determination portion determines a length of a distal end portion of the endoscope insertion portion protruding from a distal end surface of the overtube. The observation optical system observation direction determination portion determines vertical and lateral observation directions of the observation optical system included in the endoscope insertion portion. The manipulator protrusion amount determination portion determines a protrusion amount from the distal end surface of the overtube so that the first joint of the driving portion provided in the manipulator insertion portion is placed within an observation range of the observation optical system. The joint driving direction determination portion determines the first shaft of the first joint and the second shaft of the second joint of the driving portion provided in the manipulator insertion portion in an observation direction of the observation optical system.

BRIEF DESCRIPTION OF THE DRAWINGS

FIGS. 2 to 13 illustrate an embodiment of the present invention;
FIG. 2 illustrates a configuration of an endoscope system;
FIG. 3 illustrates a configuration of an endoscope;
FIG. 4 illustrates a manipulator apparatus including a plurality of joints;
FIG. 5 illustrates joints provided in a grasping manipulator including a hand arm on a joint piece located at a most distal end;
FIG. 6 illustrates joints provided in a high frequency manipulator including a knife arm on a joint piece located at a most distal end;
FIG. 7 illustrates a configuration of an overtube;
FIG. 8 is a sectional view taken along the line VIII-VIII in FIG. 7;
FIG. 9 illustrates a relationship between a positioning ring and an endoscope;
FIG. 10 illustrates a longitudinal positional relationship among the endoscope, a grasping tool, and an electric knife passed through the overtube;
FIG. 11 illustrates a vertical and lateral relationship among the endoscope, the grasping tool, and the electric knife passed through the overtube;
FIG. 12 illustrates operations of the endoscope, the grasping tool, and the electric knife passed through the overtube;
FIG. 13 shows a variant of an overtube and illustrates a configuration of an overtube including a through hole for a treatment instrument channel in addition to through holes through which an endoscope including an observation optical system, a grasping tool, and an electric knife are passed;
FIGS. 14 to 17 illustrate an external overtube as another exemplary configuration of an overtube;
FIG. 14 shows an endoscope and an overtube mounted to an endoscope insertion portion;
FIG. 15 is a front view of an overtube including an endoscope tube and two manipulator tubes;
FIG. 16 is a side view of an overtube with a sectional view of the manipulator tube;
FIG. 17A is a front view illustrating a configuration of a manipulator insertion portion passed through the manipulator tube;
and
FIG. 17B is a sectional view taken along the line XVIIB-XVIIB in FIG. 17A.

DETAILED DESCRIPTION OF THE PREFERRED EMBODIMENTS

Figure 1:
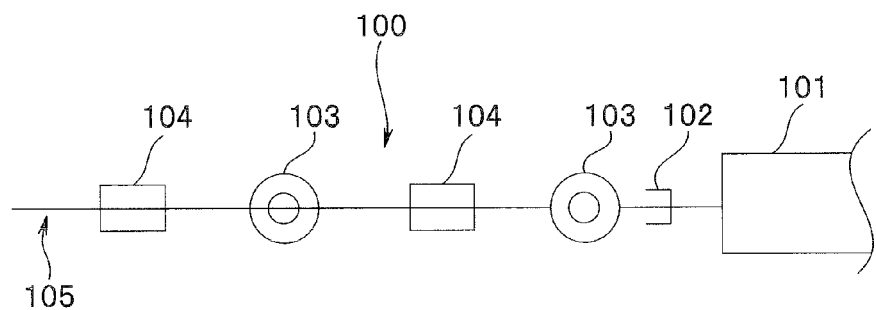
FIG. 1 illustrates an exemplary configuration of a joint of a multijoint knife.

Now, an embodiment of the present invention will be described with reference to the drawings.

As shown in FIG. 2, an endoscope system 1 includes an electronic endoscope (hereinafter simply referred to as an endoscope) 2, an overtube 3, a plurality of manipulator apparatuses 4 (a grasping manipulator 4A and a high frequency manipulator 4B described later in the present embodiment), a support base 5, a manipulator operation apparatus 6, an endoscope light source apparatus 7, a video processor 8, a control device 9, a high frequency power supply apparatus 10, and display apparatuses 11 and 12.

The support base 5 includes a column 5a. A table 5b is secured to the column 5a. A vertical arm 5c stands on an upper surface of the table 5b. The vertical arm 5c is mounted to the table 5b rotatably clockwise and counterclockwise. A first arm holding member 5e is provided on the vertical arm 5c, for example, via a plurality of securing members 5d. Reference numeral 5f denotes an L-shaped arm, which includes a vertical arm portion 5g and a horizontal arm portion 5h. The vertical arm portion 5g is rotatably mounted to the first arm holding member 5e. A second arm holding member 5i is provided on the horizontal arm portion 5h. An endoscope holding arm 5k that holds the endoscope 2 is rotatably mounted to the second arm holding member 5i.

Manipulator drive units 5U1 and 5U2 are provided on the upper surface of the table 5b. In the manipulator drive units 5U1 and 5U2, a plurality of drive motors (not shown) that pull and release a plurality of angle wires 5l, or drive motors that move the manipulators 4A and 4B forward and backward are provided. A manipulator control box 5m is provided, for example, underneath the lower surface of the table 5b. A control circuit (not shown) that controls the plurality of drive motors in the manipulator drive units 5U1 and 5U2 is provided in the manipulator control box 5m. The manipulator control box 5m is electrically connected to the manipulator operation apparatus 6 and the control device 9, for example, via signal cables.

Reference numeral 4c denotes a high frequency manipulator handle (hereinafter referred to as a handle), which is provided on the high frequency manipulator 4B. The handle 4c is connected to the high frequency power supply apparatus 10 via an electric cable. The handle 4c supplies high frequency power, and performs operations of housing and protruding a distal end electrode described later.

Figure 3:
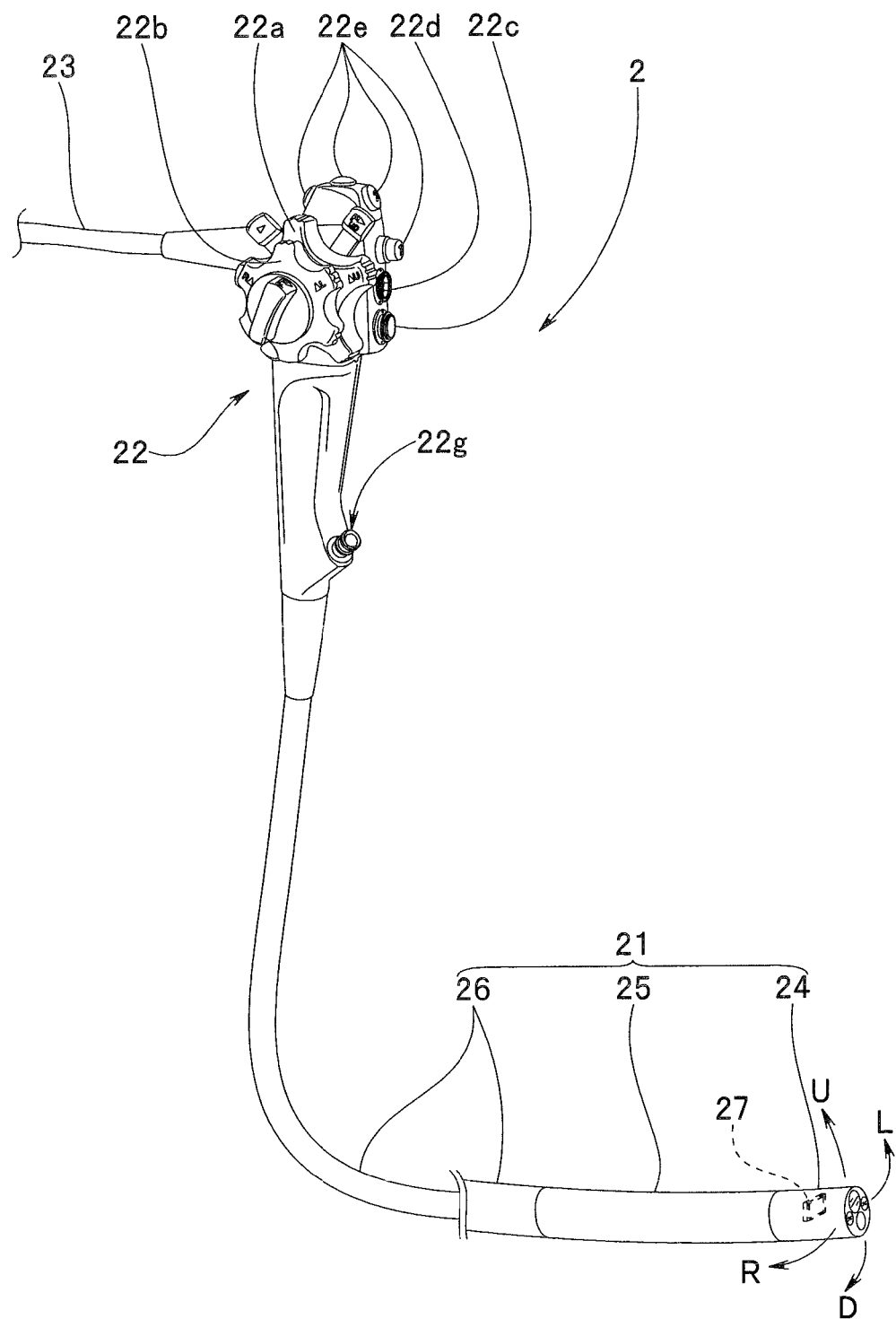

As shown in FIG. 3, the endoscope 2 includes an endoscope insertion portion 21 to be inserted into a body, an operation portion 22 provided on a proximal end side of the endoscope insertion portion 21, and a universal cord 23 extending from the operation portion 22. The endoscope insertion portion 21 is passed through a below described endoscope hole (reference numeral 31 in FIG. 7) provided in the overtube 3. A proximal end portion of the universal cord 23 is connected to the endoscope light source apparatus 7 and the video processor 8 in FIG. 2.

The video processor 8 includes a drive circuit for driving a below described solid-state image pickup device (hereinafter simply referred to as an image pickup device), and an image processing circuit that receives an image signal photoelectrically converted by the image pickup device and transmitted and generates a video signal. The video signal generated by the image processing circuit is outputted to the display apparatuses 11 and 12. The display apparatuses 11 and 12 receive the video signal, and endoscope images are displayed on screens 11a and 12a of the display apparatuses 11 and 12.

The endoscope insertion portion 21 includes a rigid distal end portion 24, a bending portion 25 bendable in vertical and lateral directions, and a long flexible tube 26 connected in order from a distal end side. The operation portion 22 also serves as a grasping portion, and includes a vertical bending knob 22a, a lateral bending knob 22b, an air/water feeding button 22c, a suction button 22d, and various operation buttons 22e. The vertical bending knob 22a bends the bending portion 25 and directs an observation window (see reference numeral 24a in FIG. 11) provided in the distal end portion 24 upward (in a U direction in FIG. 3) or downward (in a D direction in FIG. 3). The lateral bending knob 22b bends the bending portion 25 and directs the observation window 24a provided in the distal end portion 24 leftward (in an L direction in FIG. 3) or rightward (in an R direction in FIG. 3). The operation portion 22 includes a treatment instrument passing opening 22g through which a treatment instrument is inserted into a treatment instrument channel (not shown).

The distal end portion 24 includes therein an image pickup apparatus that constitutes an observation optical system. In the image pickup apparatus, an image pickup unit is provided including a light receiving surface on which an optical image having passed through an unshown objective optical unit is formed. In the image pickup unit, an image pickup device 27 such as a CCD (Charge Coupled Device) or a CMOS (Complementary Metal-Oxide Semiconductor) is provided.

The light receiving surface of the image pickup device 27 is placed perpendicularly to an insertion axis of the endoscope insertion portion 21. Endoscope images picked up by the image pickup apparatus are displayed on the screens 11a and 12a of the display apparatuses 11 and 12. A vertical transfer direction (a direction of arrow V in FIG. 11) of the image pickup device 27 matches a vertical direction of the screens 11a and 12a of the display apparatuses 11 and 12, and a lateral direction matches a horizontal transfer direction (a direction of arrow H in FIG. 11) of the image pickup device 27. Specifically, the vertical and lateral directions of the endoscope image picked up by the image pickup apparatus match the vertical and lateral directions of the endoscope images displayed on the screens 11a and 12a.

Vertical and lateral directions of the bending portion 25 that constitutes the endoscope insertion portion 21 are set correspondingly to the vertical and lateral directions of the endoscope images displayed on the screens 11a and 12b of the display apparatuses 11 and 12. Specifically, the vertical and lateral directions of the bending portion 25 correspond to the vertical and lateral directions of the endoscope images displayed on the screens 11a and 12a of the display apparatuses 11 and 12. Thus, for example, when an operator operates the vertical bending knob 22a to bend the bending portion 25 upward, the bending portion 25 is bent upward by the operation and the endoscope images are changed so that an upward direction of the endoscope images displayed on the screens 11a and 12a is observed.

The video processor 8 and the display apparatuses 11 and 12 are connected via video cables (not shown).

As shown in FIG. 2, the endoscope system 1 of the present embodiment includes the manipulators 4A and 4B. The grasping manipulator (hereinafter referred to as a grasping tool) 4A includes a hand arm 4h, and the high frequency manipulator (hereinafter referred to as an electric knife) 4B includes a knife arm 4k as a distal end electrode. The grasping tool 4A and the electric knife 4B are passed through below described two manipulator holes (reference numerals 32 and 33 in FIG. 7) provided in the overtube 3.

Figure 4:
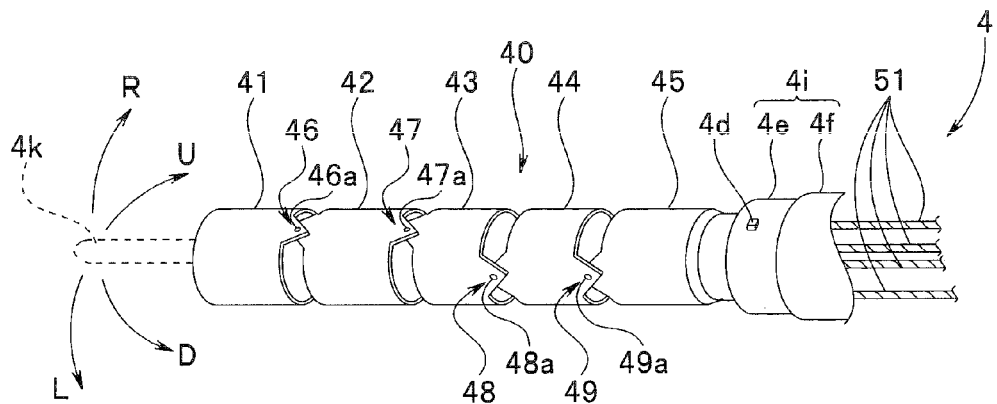

As shown in FIG. 4, the grasping portion tool 4A and the electric knife 4B each include a driving portion 40 on a distal end side of an elongated manipulator insertion portion 4i. The manipulator insertion portion 4i includes an insertion portion distal end piece 4e and a flexible tube 4f.

The driving portion 40 includes, for example, five joint pieces 41, 42, 43, 44 and 45, and adjacent joint pieces are connected rotatably clockwise and counterclockwise around connection shafts 46a, 47a, 48a and 49a. In the present embodiment, the connection shafts 46a and 47a constitute a first shaft parallel to an X-axis in FIGS. 4 and 5, and the connection shafts 48a and 49a constitute a second shaft parallel to a Y-axis.

Figure 5:
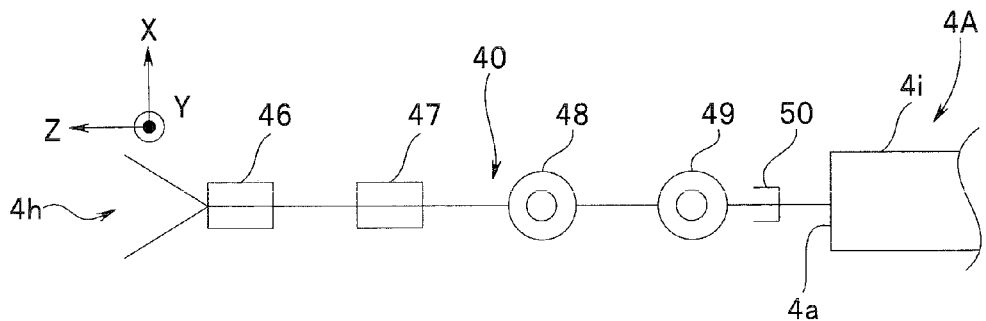
Figure 6:
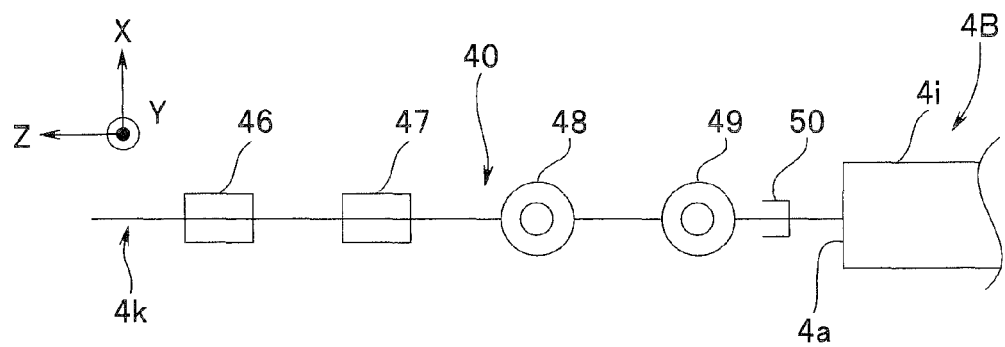

As shown in FIGS. 4 to 6, the first joint piece 41 and the second joint piece 42 are rotatably connected by the first connection shaft 46a to constitute a yaw drive joint as a first joint. Similarly, the second joint piece 42 and the third joint piece 43 are connected by the second connection shaft 47a to constitute a yaw drive joint. The third joint piece 43 and the fourth joint piece 44 are connected by the third connection shaft 48a to constitute a pitch drive joint as a second joint, and the fourth joint piece 44 and the fifth joint piece 45 are connected by the fourth connection shaft 49a to constitute a pitch drive joint.

The grasping tool 4A in FIG. 5 includes the hand arm 4h on a distal end side of the first joint piece 4l located at a most distal end. On the other hand, the electric knife 4B in FIG. 6 includes the knife arm 4k on a distal end side of the first joint piece 4l located at a most distal end.

In the present embodiment, on the distal end side of the insertion portion distal end piece 4e that constitutes each of the grasping tool 4A and the electric knife 4B, the second pitch drive joint 49 and a first pitch drive joint 48 as a second joint that rotates around the second shaft, and a second yaw drive joint 47 and a first yaw drive joint 46 as a first joint that rotates around the first shaft are provided in order.

A distal end of a predetermined wire 51 among the plurality of angle wires 51 extending from the manipulator drive units 5U1 and 5U2 is secured to each of the joints 46, 47, 48 and 49 at two predetermined diagonal positions. The plurality of angle wires 51 are pulled and released by unshown drive motors corresponding to the joints 46, 47, 48 and 49 to which the angle wires 51 provided in the manipulator drive units 5U1 and 5U2 are connected.

Reference numeral 50 denotes a prismatic drive joint. The prismatic drive joint 50 moves the hand arm 4h and the knife arm 4k forward and backward in a Z-axis direction. The grasping tool 4A includes a roll drive joint (not shown) that rotates the hand arm 4h around the Z-axis direction.

In the present embodiment, the pitch drive joints 48 and 49 are rotated around the Y-axis, and thus, for example, the knife arm 4k shown by a broken line in FIG. 4 is moved in the U direction or the D direction corresponding to the vertical direction of the bending portion 25. On the other hand, the yaw drive joints 46 and 47 are rotated around the X-axis, and thus the knife arm 4k is moved in the L direction or the R direction corresponding to the lateral direction of the bending portion 25.

Specifically, a position and an attitude of the hand arm 4h included in the grasping tool 4A are changed with changes of joint angles of the yaw drive joints 46 and 47 and the pitch drive joints 48 and 49, axially forward and backward movement by the prismatic drive joint 50, and rotation of the roll drive joint. On the other hand, a position and an attitude of the knife arm 4k included in the electric knife 4B are changed with changes of joint angles of the yaw drive joints 46 and 47 and the pitch drive joints 48 and 49, and axially forward and backward movement by the prismatic drive joint 50.

The position and the attitude of the hand arm 4h are changed by appropriately operating a grasping tool master portion 6A provided in the manipulator operation apparatus 6 in FIG. 2. On the other hand, the position and the attitude of the knife arm 4k in the electric knife 4B are changed by appropriately operating an electric knife master portion 6B provided in the manipulator operation apparatus 6.

The master portions 6A and 6B are input apparatuses for setting joint angles of the joints 46, 47, 48 and 49 of the grasping tool 4A and the electric knife 4B or an axial position of the joint 50. The master portions 6A and 6B as the input apparatuses are slidably mounted to holding portions 60a and 60b provided on a stand 60.

The grasping tool master portion 6A includes a master side hand arm 6h and master side joint pieces 61, 62, 63, 64 and 65 corresponding to the hand arm 4h and the joint pieces 41, 42, 43, 44 and 45 of the grasping tool 4A. The five master side joint pieces 61, 62, 63, 64 and 65 are connected by master side yaw drive joints 66 and 67 and master side pitch drive joints 68 and 69.

On the other hand, the electric knife master portion 6B includes a master side knife arm 6k and master side joint pieces 61, 62, 63, 64 and 65 corresponding to the knife arm 4k and the joint pieces 41, 42, 43, 44 and 45 of the electric knife 4B. The five master side joint pieces 61, 62, 63, 64 and 65 are also connected by master side yaw drive joints 66 and 67 and master side pitch drive joints 68 and 69.

The grasping tool master portion 6A and the electric knife master portion 6B are operated by an operator 19 standing, for example, between the grasping tool master portion 6A and the electric knife master portion 6B as shown by broken lines.

The operator 19 operates the master side joint pieces 61, 62, 63, 64 and 65 of the grasping tool master portion 6A or the electric knife master portion 6B as required, and thus joint angles of the master side yaw drive joints 66 and 67, joint angles of the master side pitch drive joints 68 and 69, or the axial position of the master side prismatic drive joint 70 are changed to change the position or the attitude of the hand arm 4h or the knife arm 4k.

Movements of the master side joint pieces 61, 62, 63, 64 and 65 are detected by a sensor (not shown) as angle change amounts of the master side yaw drive joints 66 and 67, angle change amounts of the master side pitch drive joints 68 and 69, or an axial movement amount of the master side prismatic drive joint 70. The angle change amounts of the joints 66, 67, 68 and 69 and the movement amount of the joint 70 detected by the sensor are outputted as drive operation information from the master portions 6A and 6B to the manipulator control box 5m via a signal cable 18.

The drive operation information inputted to the manipulator control box 5m is outputted to the control device 9. Then, an unshown CPU of the control device 9 calculates the angle change amounts of the joints 46, 47, 48 and 49 of the grasping tool 4A and the electric knife 4B, and calculates the axial movement amount of the prismatic drive joint 50.

Then, the control device 9 outputs control signals corresponding to the angle change amounts and the movement amount to the manipulator control box 5m to drive the drive motors provided in the manipulator drive units 5U1 and 5U2. Thus, the angle wires 51 corresponding to the joints 46, 47, 48 and 49 are pulled and released to change the angles of the joints 46, 47, 48 and 49 or the axial position of the joint 50. Specifically, the position and the attitude of the hand arm 4h of the grasping tool 4A or the position and the attitude of the knife arm 4k of the electric knife 4B are changed according to instructions from the master portions 6A and 6B.

In the present embodiment, the two yaw drive joints and the two pitch drive joints are provided in order from the distal end side on each of the grasping tool 4A, the electric knife 4B, and the master portions 6A and 6B. However, the number of the yaw drive joints and the number of the pitch drive joints are not limited to two. The number of the joint pieces of the master portion is not limited to five. The number of the yaw drive joints and the pitch drive joints each may be more than or less than two as long as the yaw drive joints and the pitch drive joints are placed in order from the distal end side.

In the present embodiment, the input apparatus is the master portion, but the input apparatus is not limited to the master portion. Specifically, a known input apparatus can be used such as a keyboard, a touch pen, or a joystick that can set a desired operation.

Figure 7:
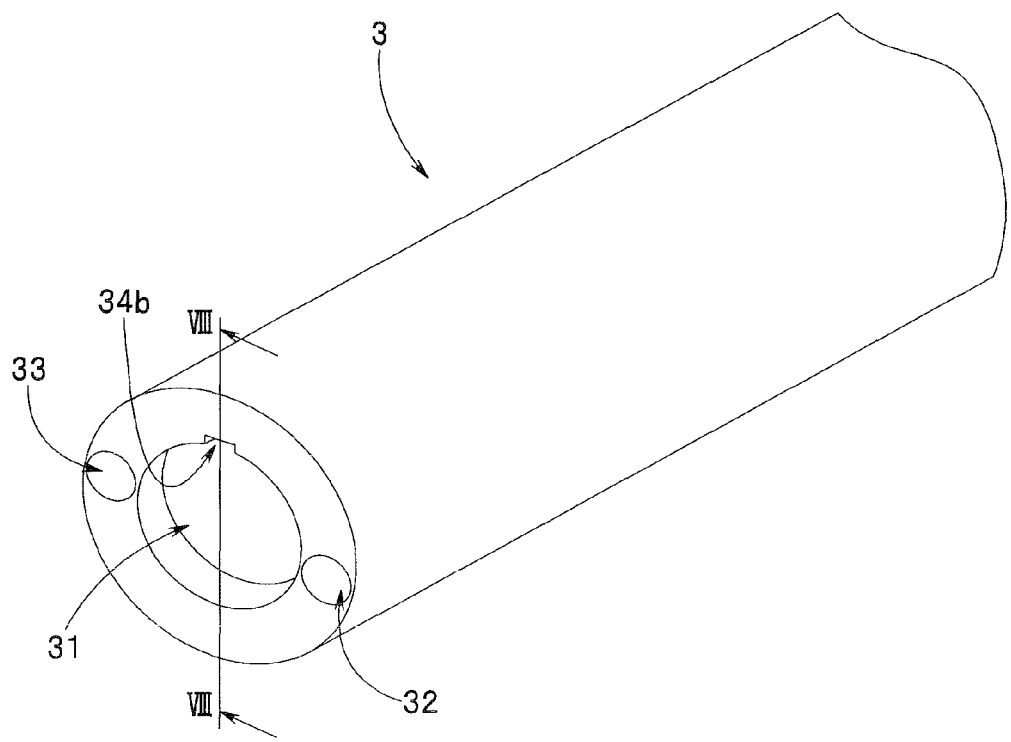

The overtube 3 in the present embodiment in FIG. 7 is a flexible multi-lumen tube. The overtube 3 includes through holes 31, 32 and 33 parallel to the longitudinal axis. The through hole 31 is an endoscope insertion portion passing hole (hereinafter the through hole 31 is referred to as an endoscope hole 31) through which the endoscope insertion portion 21 of the endoscope 2 is passed. The through holes 32 and 33 are manipulator passing holes (hereinafter referred to as manipulator holes) through which the manipulator insertion portion 4i of the grasping tool 4A or the manipulator insertion portion 4i of the electric knife 4B is passed. In the present embodiment, the through hole 32 is, for example, a manipulator hole 32, through which the manipulator insertion portion 4i of the grasping tool 4A is passed. The through hole 33 is, for example, a manipulator hole 33, through which the manipulator insertion portion 4i of the electric knife 4B is passed.

Figure 8:
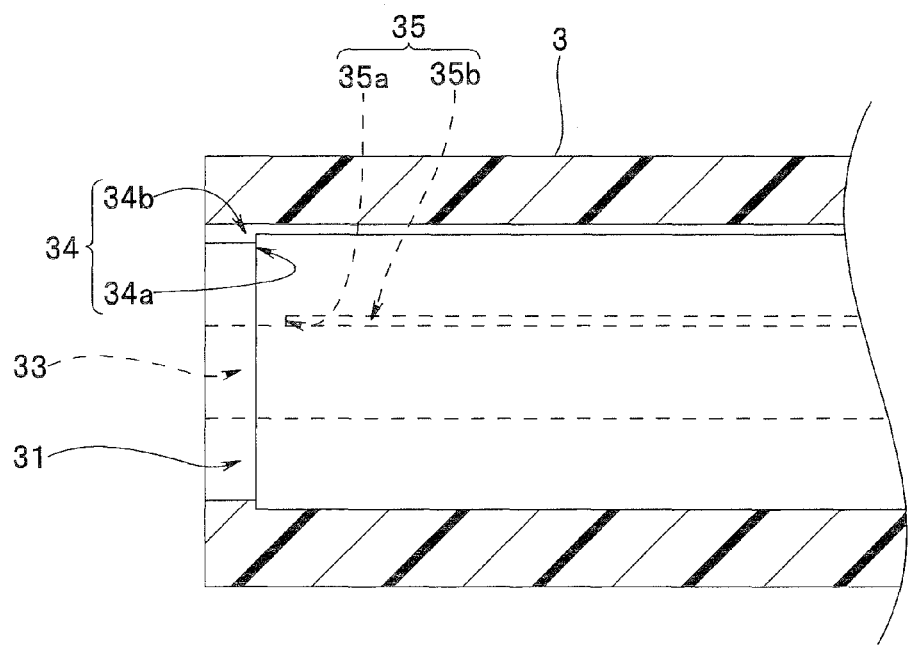

As shown in FIG. 8, the endoscope hole 31 includes an endoscope positioning portion 34 on a distal end side. The endoscope positioning portion 34 includes an abutment step 34a as an endoscope protrusion amount determination portion, and a first recessed portion 34b as an observation optical system observation direction determination portion.

Figure 11:
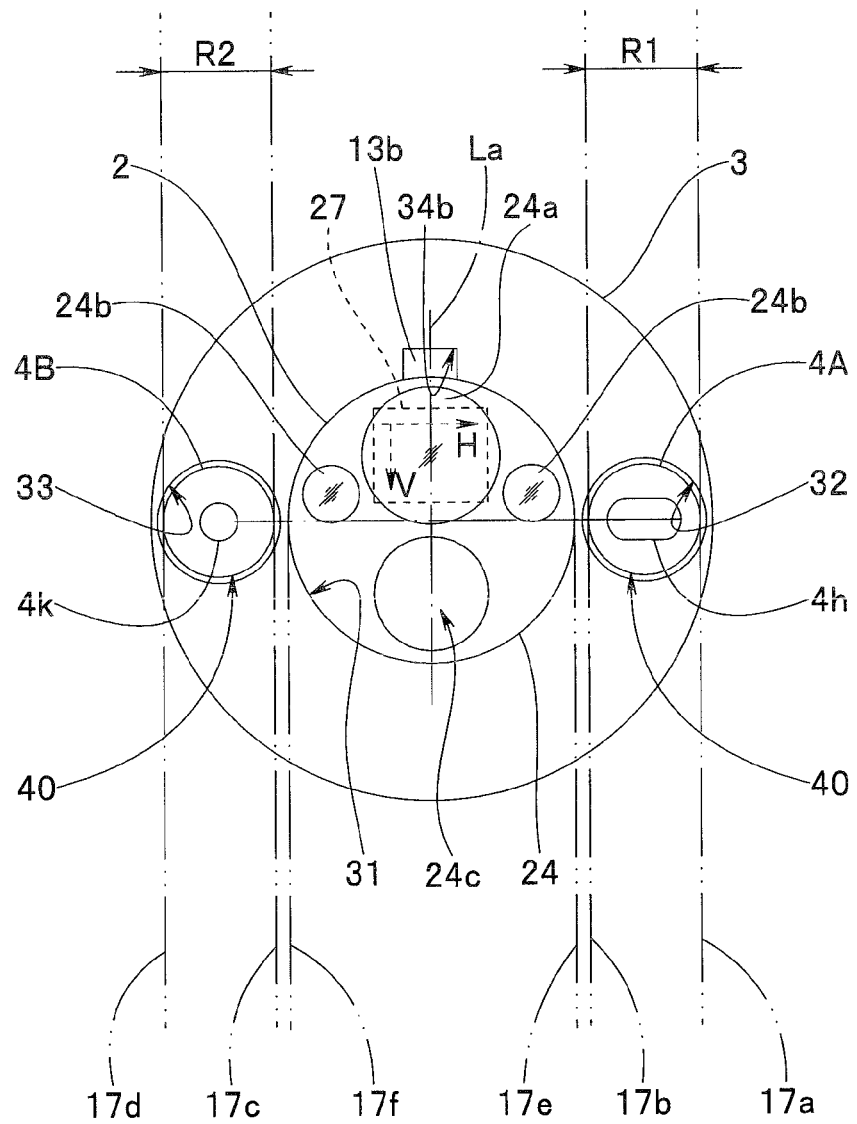

The manipulator holes 32 and 33 each include a manipulator positioning portion 35 on a distal end side. The manipulator positioning portion 35 includes an abutment surface 35a as a manipulator protrusion amount determination portion, and a second recessed portion 35b as a joint driving direction determination portion. The first recessed portion 34b and the second recessed portion 35b are provided correspondingly to each other. Specifically, when the first recessed portion 34b of the endoscope hole 31 is provided at a twelve o'clock position as shown in FIG. 11, the second recessed portion 35b of each of the manipulator holes 32 and 33 is also provided at the twelve o'clock position. When the first recessed portion 34b is provided at a six o'clock position in FIG. 11, the second recessed portion 35b is also provided at the six o'clock position.

Figure 9:
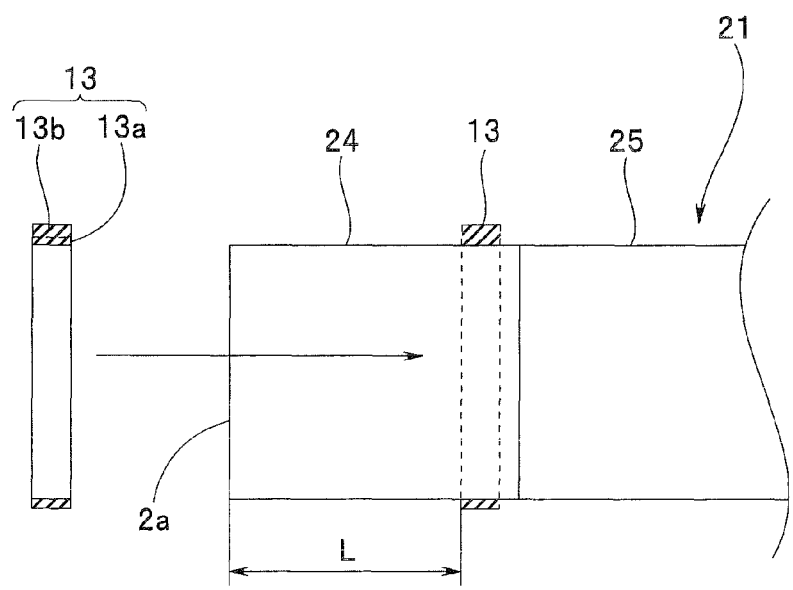

On the distal end portion 24 of the endoscope insertion portion 21 of the endoscope 2, for example, an annular positioning ring 13 is secured as shown in FIG. 9. The positioning ring 13 includes an annular portion 13a and a protruding portion 13b. The annular portion 13a serves as both an endoscope protrusion amount determination portion and a mounting portion. The annular portion 13a has an inner diameter, for example, sized to fit around the distal end portion 24 by a predetermined adhesion force, and an outer diameter sized to engage in the abutment step 34a.

The protruding portion 13b is an observation optical system observation direction determination portion, and protrudes from an outer peripheral surface of the annular portion 13a with a predetermined width by a predetermined amount. The width and the protrusion amount of the protruding portion 13b are set in view of a width and a depth of the first recessed portion 34b. The positioning ring 13 is located at a predetermined distance L from a distal end surface 2a of the endoscope 2. At this time, the protruding portion 13b is located above the image pickup device 27.

On the insertion portion distal end piece 4e that constitutes the manipulator insertion portion 4i of each of the grasping tool 4A and the electric knife 4B, a projecting portion (see reference numeral 4d in FIG. 4) is provided. The projecting portion 4d is provided on a line extending from a line connecting the connection shaft 46a of the first yaw drive joint 46 on an upper side and the connection shaft 47a of the second yaw drive joint 47 on the upper side. The projecting portion 4d serves as both a manipulator protrusion amount determination portion and a joint driving direction determination portion, engages in the second recessed portion 35b of the manipulator positioning portion 35 formed in each of the manipulator holes 32 and 33, and has a distal end surface that abuts against the abutment surface 35a.

In the present embodiment, the projecting portion 4d is provided on the insertion portion distal end piece 4e, but a positioning ring including an annular portion and a protruding portion as described above may be secured on the insertion portion distal end piece 4e.

In the present embodiment, the positioning ring 13 including the annular portion 13a and the protruding portion 13b is secured on the endoscope insertion portion 21 of the endoscope 2. However, a projecting portion may be previously provided on the endoscope insertion portion 21.

A positional relationship among the endoscope 2, the grasping tool 4A, and the electric knife 4B will be described with reference to FIGS. 10 and 11. The endoscope insertion portion 21 on which the positioning ring 13 is secured in a predetermined state is passed through the endoscope hole 31 in the overtube 3, the manipulator insertion portion 4i of the grasping tool 4A is passed through the manipulator hole 32, and the manipulator insertion portion 4i of the electric knife 4B is passed through the manipulator hole 33.

First, with reference to FIG. 10, a longitudinal positional relationship among the endoscope 2, the grasping tool 4A, and the electric knife 4B passed through the overtube 3 will be described.

When the endoscope 2, the grasping tool 4A, and the electric knife 4B are passed through the holes 31, 32 and 33 in the overtube 3 in a predetermined state, in the endoscope 2, the annular portion 13a abuts against the abutment step 34a to enter a predetermined arrangement state. In the arrangement state, the distal end portion 24 of the endoscope 2 protrudes from the distal end surface 3a of the overtube 3 by a predetermined amount (for example, L1).

In each of the grasping tool 4A and the electric knife 4B, the projecting portion 4d abuts against the abutment surface 35a, and each of the hand arm 4h and the knife arm 4k protrudes from the distal end surface 3a of the overtube 3 by a predetermined amount. In the protrusion state, the first yaw drive joint 46 and the second yaw drive joint 47 that constitute the driving portion 40 protrude from the distal end surface 2a of the endoscope 2 and are placed within an endoscope observation range 20 in the present embodiment.

As such, the distal end portion 24 of the endoscope 2 and the driving portions 40 of each of the grasping tool 4A and the electric knife 4B are protruded from the distal end surface 3a of the overtube 3 in a predetermined state. In this case, as compared with the case where the two yaw drive joints 46 and 47 as well as the two pitch drive joints 48 and 49 are protruded from the distal end surface 2a of the endoscope 2, a distance between the observation window 24a of the endoscope 2 and the area to be treated with the grasping tool 4A and the electric knife 4B can be reduced. Thus, the image of the area to be treated is displayed in a high size ratio with respect to sizes of the screens 11a and 12a of the display apparatuses 11 and 12, thereby allowing efficient treatment.

Next, with reference to FIG. 11, a vertical and lateral positional relationship among the endoscope 2, the grasping tool 4A, and the electric knife 4B passed through the overtube will be described.

When the endoscope 2 is passed through the hole 31 in the overtube 3 in the predetermined state, the protruding portion 13b on the endoscope 2 engages in the first recessed portion 34b. Then, the endoscope 2 is mounted to the overtube 3 with the horizontal transfer direction of the image pickup device 27 included in the distal end portion 24 in a direction of an arrow H, and the vertical transfer direction in a direction of an arrow V.

Specifically, for the overtube 3 in which the endoscope 2 is provided, the side of the first recessed portion 34b is an upward direction. Reference numeral 24b denotes an illumination window, and reference numeral 24c denotes an opening of a treatment instrument channel.

When the grasping tool 4A and the electric knife 4B are passed through the holes 32 and 33 in the overtube 3 in the predetermined state, the projecting portion 4d on each of the grasping tool 4A and the electric knife 4B engages in the second recessed portion 35b. Then, the connection shafts 46a and 47a of the yaw drive joints 46 and 47 of each of the grasping tool 4A and the electric knife 4B are placed in parallel with the vertical transfer direction, and the connection shafts 48a and 49a of the pitch drive joints 48 and 49 are placed in parallel with the horizontal transfer direction. As described above, the first yaw drive joint 46 and the second yaw drive joint 47 of the driving portion 40 protrude from the distal end surface 2a of the endoscope 2.

Thus, the connection shafts 46a and 47a of the yaw drive joints 46 and 47 of each of the grasping tool 4A and the electric knife 4B are directed with reference to the vertical transfer direction of the image pickup device 27, and the connection shafts 48a and 49a of the pitch drive joints 48 and 49 are directed with reference to the horizontal transfer direction of the image pickup device 27. The pitch drive joints 48 and 49 of each of the grasping tool 4A and the electric knife 4B are not displayed in the endoscope images displayed on the screens 11a and 12a of the display apparatuses 11 and 12.

Figure 10:
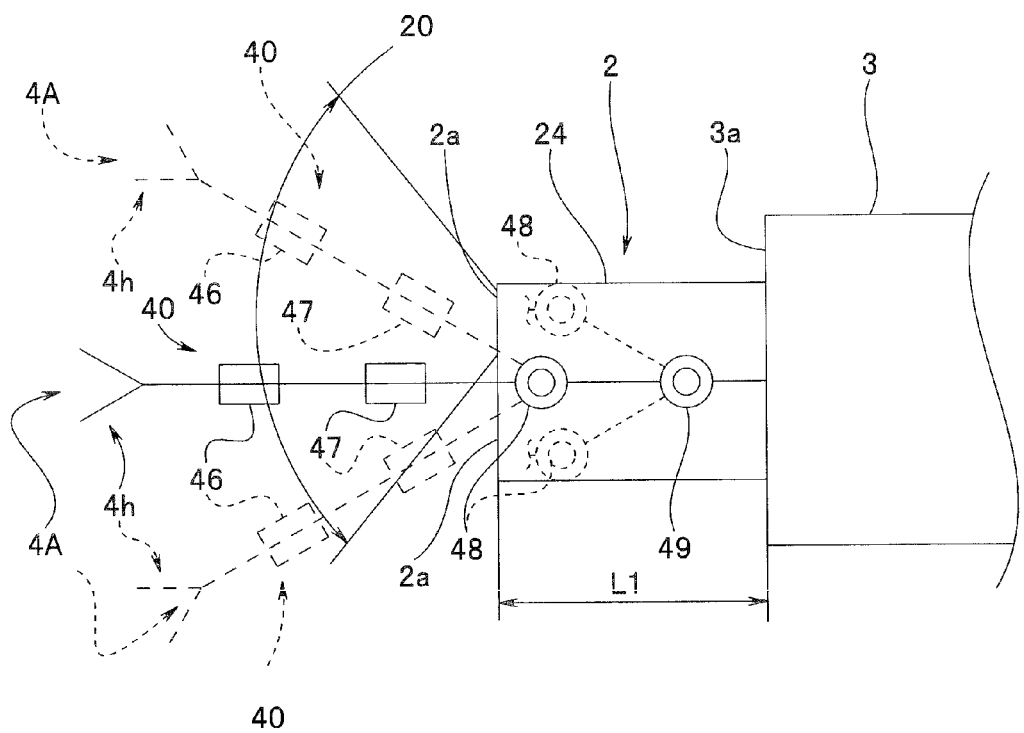

In this state, the pitch drive joints 48 and 49 are rotated, for example, as shown by broken lines in FIG. 10. Then, the hand arm 4*h*, the knife arm 4*k*, and the joint pieces 41, 42, 43 and 44 are moved within a first range R1 and a second range R2 in FIG. 11. Phantom lines 17*a* and 17*b* defining the first range R1 are a first tangent and a second tangent to the manipulator hole 32, parallel to the vertical transfer direction and parallel to an axis La that is one axis of a central axis of the endoscope hole 31. Phantom lines 17*c* and 17*d* defining the second range R2 are a first tangent and a second tangent to the manipulator hole 33, parallel to the axis La.

The phantom line 17*b* is located outside a phantom line 17*e* parallel to the axis La of the endoscope hole 31, and the phantom line 17*c* is located outside a phantom line 17*f* facing and parallel to the phantom line 17*e*.

Thus, for example, even if the pitch drive joints 48 and 49 that are not displayed in the endoscope images are operated, the driving portions 40 of the grasping tool 4A and the electric knife 4B are prevented from being brought into contact with the endoscope 2 protruding from the overtube 3.

Endoscopic submucosal dissection with the endoscope system 1 including the endoscope 2, the overtube 3, the grasping tool 4A, and the electric knife 4B configured as described above will be described.

A user first mounts the positioning ring 13 on the distal end portion 24 of the endoscope 2 in a predetermined positional relationship.

Then, the user places the endoscope insertion portion 21 of the endoscope 2 on which the positioning ring 13 is secured in the endoscope hole 31 in the overtube 3 in a predetermined state.

An operator inserts the overtube 3 through which the endoscope 2 is passed into the body while observing the endoscope image displayed, for example, on the screen 11*a* of the display apparatus 11. Then, a bending mechanism or the like provided in the endoscope 2 is used to cause the distal end portion 24 of the endoscope 2 to face the area to be treated.

Then, the operator introduces a needle knife from the treatment instrument passing opening 22*g* provided in the endoscope 2 via the treatment instrument channel near to the area to be treated. Then, the operator marks a lesion while observing the endoscope image displayed on the screen 11*a*. The operator checks the mark, and then removes the needle knife from the treatment instrument channel of the endoscope 2.

Then, the operator introduces a local injection needle via the treatment instrument channel of the endoscope 2 near to the area to be treated. Then, the operator injects physiological saline into the marked lesion to expand the lesion while observing the endoscope image displayed on the screen 11*a*. The operator checks the expansion of the lesion, and then removes the local injection needle from the treatment instrument channel.

Then, the operator inserts the manipulator insertion portion 4*i* of the electric knife 4B into the manipulator hole 33. Then, the operator places the manipulator insertion portion 4*i* in the manipulator hole 33 in a predetermined state. Then, the knife arm 4*k* and the yaw drive joints 46 and 47 of the electric knife 4B are displayed in the endoscope image displayed on the screen 11*a*.

Then, the operator operates the joint pieces 61, 62, 63, 64 and 65 of the master portion 6B to perform full circumferential dissection along the mark. At this time, as described above, the connection shafts 48*a* and 49*a* of the pitch drive joints 48 and 49 are parallel to the horizontal transfer direction of the image pickup device 27 provided in the endoscope 2, and thus the dissection can be performed so that the driving portion 40 of the electric knife 4B protruding from the overtube 3 is not brought into contact with the endoscope 2 protruding from the overtube 3.

Next, the operator passes the manipulator insertion portion 4*i* of the grasping tool 4A through the manipulator hole 32. Then, the operator places the manipulator insertion portion 4*i* in the manipulator hole 32 in a predetermined state. Then, the hand arm 4*h* and the yaw drive joints 46 and 47 of the grasping tool 4A are displayed in the endoscope image displayed on the screen 11*a*.

The operator operates the joint pieces 61, 62, 63, 64 and 65 of the master portion 6B to adjust the knife arm 4*k* and the joint pieces 41 and 42 to be substantially parallel to mucosa while observing the endoscope image displayed on the screen 11*a*. The operator also operates the joint pieces 61, 62, 63, 64 and 65 of the master portion 6A, and rotates the roll drive joint of the grasping tool 4A around the Z-axis to adjust the hand arm 4*h* to a desired direction while observing the endoscope image displayed on the screen 11*a*. Then, the operator operates the hand arm 4*h* to grasp the mucosa fully circumferentially dissected.

Also at this time, the connection shafts 48*a* and 49*a* of the pitch drive joints 48 and 49 are parallel to the horizontal transfer direction of the image pickup device 27 provided in the endoscope 2. Thus, during the above described operation, the hand arm 4*h* and the knife arm 4*k* are moved so that the joint pieces 44 and 45 of the grasping tool 4A and the electric knife 4B that are not displayed in the endoscope image are not brought into contact with the endoscope 2.

Figure 12:
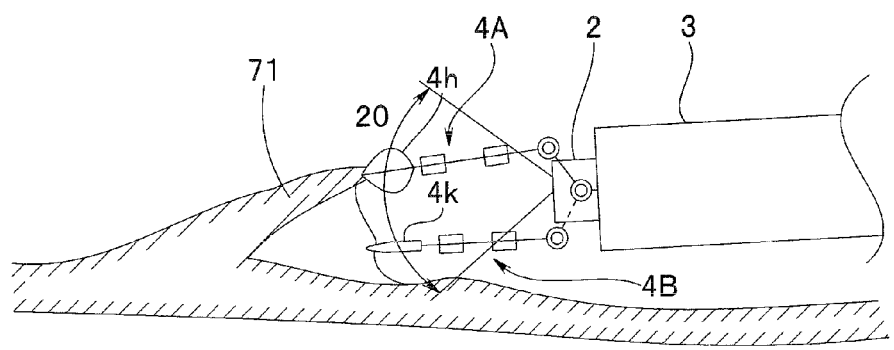

Then, the operator operates appropriately the master portions 6A and 6B to lift the mucosa 71 grasped by the hand arm 4*h* as shown in FIG. 12. Then, the operator operates appropriately the master portions 6A and 6B to apply counter traction to the grasped mucosa 71, and move the knife arm 4*k* to gradually dissect the mucosa 71.

When limited operation ranges of the joints 46, 47, 48 and 49 of the grasping tool 4A and the electric knife 4B prevent movement of the hand arm 4*h* or the knife arm 4*k* and make it difficult to advance dissection, the bending portion 25 of the endoscope 2 is bent or the endoscope insertion portion 21 is moved forward and backward to move the knife arm 4*k* to a position where dissection can be performed.

Then, the operator operates appropriately the master portions 6A and 6B to grasp the mucosa 71 with the hand arm 4*h*, lift the mucosa grasped by the hand arm 4*h*, and move the knife arm 4*k* to advance the dissection.

After the dissection is completed, the dissected mucosa 71 grasped by the hand arm 4*h* is removed from the body together with the endoscope 2. At this time, the master portions 6A and 6B are appropriately operated to return the grasping tool 4A and the electric knife 4B to initial states and retract the hand arm 4*h* and the knife arm 4*k* into the manipulator holes 32 and 33 while the endoscope image displayed on the screen 11*a* is observed.

As such, the overtube, the endoscope passed through the overtube, and the two manipulator apparatuses passed through the overtube and including the two yaw drive joints and the two pitch drive joints arranged in order from the distal end side are prepared. Then, the endoscope insertion portion is placed in the endoscope hole in the overtube with reference to the vertical direction of the endoscope. Also, the manipulator insertion portion is passed through the manipulator hole in the overtube with the yaw drive joints and the pitch drive joints of each of the grasping tool and the electric knife in the predetermined directions. Then, the distal end portion of the endoscope protrudes from the distal end surface of the overtube by a predetermined amount, and the yaw drive joints that constitute the driving portion of each of the grasping tool and the electric knife are placed in the observation range of the endoscope, and the pitch drive joints are placed in parallel with the endoscope.

Thus, the observation window of the endoscope is located at a predetermined distance from the area to be treated, and the image of the area to be treated can be displayed in a predetermined size with respect to the size of the screen of the display apparatus. This ensures checking the image of the area to be treated for dissection.

The joint pieces operated by driving the pitch drive joints that are not displayed in the endoscope image are placed so as not to be brought into contact with the endoscope, and thus the operator can operate the master portion while focusing on the movement of the driving portion of each of the grasping tool and the electric knife displayed in the endoscope image.

Thus, using the endoscope system including the overtube, the endoscope, and the two manipulator apparatuses, even a relatively inexperienced operator can reliably and quickly perform surgery by endoscopic submucosal dissection.

In the above described endoscopic submucosal dissection, the needle knife is passed through the treatment instrument channel of the endoscope to mark the lesion. However, instead of passing the needle knife through the treatment instrument channel of the endoscope, the electric knife may be passed through the manipulator hole and operated by a master portion to make a mark. In this case, after the marking, the knife arm is at least deenergized and retracted so as not to be displayed on the screen. When the full circumferential dissection is performed, the electric knife is again placed in a predetermined state and reenergized.

Figure 13:
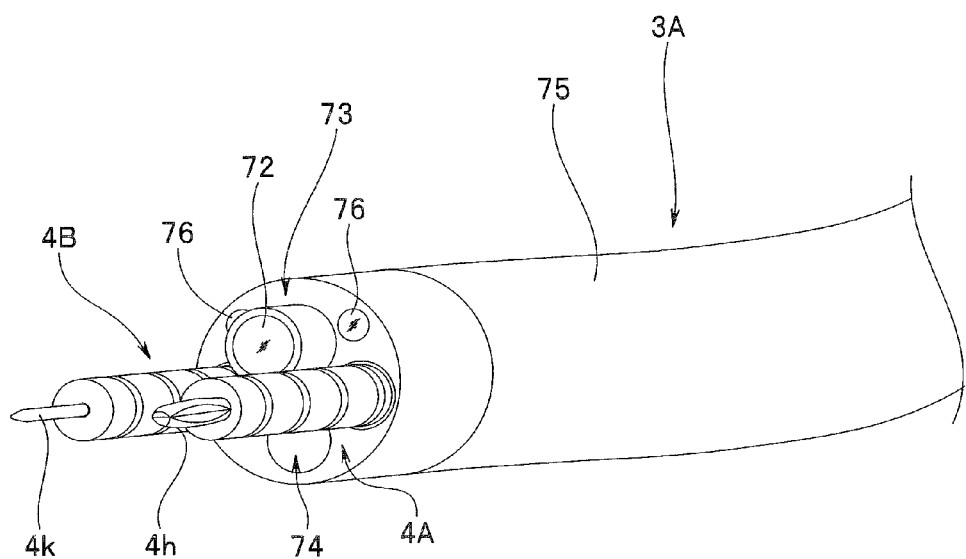

In the above described embodiment, the endoscope passed through the overtube includes the observation window, the illumination window, and the opening of the treatment instrument channel in the distal end surface. However, the endoscope may be an endoscope 73 at least including an observation optical system 72 and a flexible endoscope insertion portion as shown in FIG. 13. In this case, in addition to the holes 31, 32 and 33, a through hole 74 that constitutes a treatment instrument channel is provided in an overtube 3A through which the endoscope 73 is passed, and a bending portion 75 is provided on the overtube 3A. A through hole in which a light emitting element 76 is provided may be provided in the overtube 3A.

The overtube 3A thus configured can increase bending performance. Other configurations are the same as in the above described embodiment, and the same components are denoted by the same reference numerals and descriptions thereof will be omitted.

Further, in the above described embodiment, the overtube is the multi-lumen tube. However, the overtube is not limited to the multi-lumen tube, but may be of an external type that can be mounted to the endoscope insertion portion 21 as shown in FIGS. 14 to 17.

Figure 14:
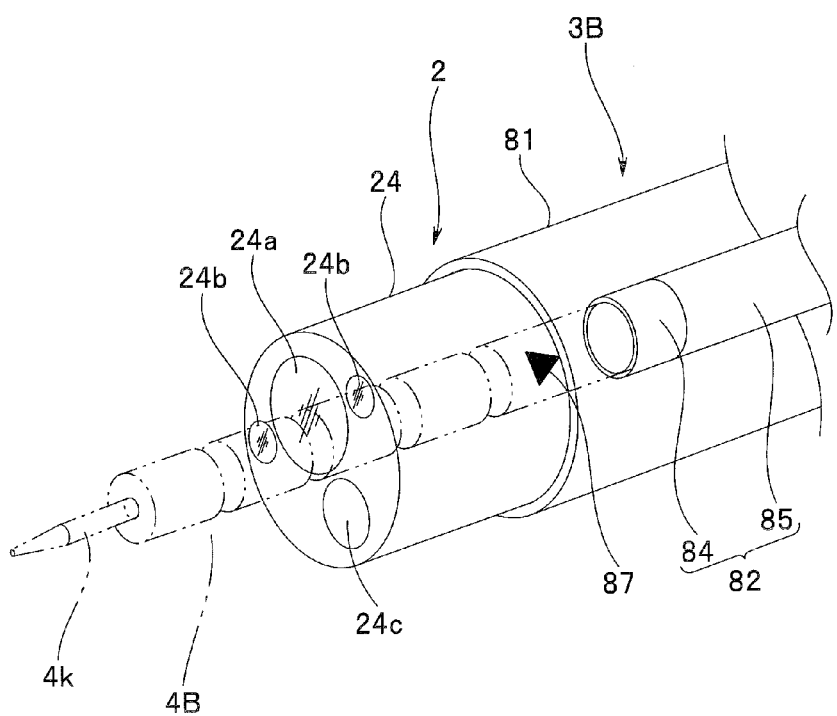

As shown in FIGS. 14 to 16, the overtube in the present embodiment is an external overtube 3B mounted to the endoscope insertion portion 21 of the endoscope 2. The external overtube 3B includes an endoscope tube 81 and manipulator tubes 82 and 83. The endoscope tube 81 is mounted to the endoscope insertion portion 21 of the endoscope 2. The manipulator insertion portion 4i of the manipulator apparatus 4 is passed through each of the manipulator tubes 82 and 83. In the present embodiment, for example, the manipulator insertion portion 4i of the electric knife 4B is passed through the first manipulator tube 82 as shown by broken lines in FIG. 14. The manipulator insertion portion 4i of the grasping tool 4A is passed through the second manipulator tube 83.

The first manipulator tube 82 and the second manipulator tube 83 are provided in parallel with the endoscope tube 81 therebetween. In the present embodiment, a center of the endoscope tube 81 and centers of the manipulator tubes 82 and 83 are aligned as shown in FIG. 15.

Distal end surfaces 82a and 83a of the manipulator tubes 82 and 83 are located in flush with a distal end surface 81a of the endoscope tube 81 or on a proximal end side of the distal end surface 81a in a longitudinal axis direction of the endoscope tube 81.

The manipulator tubes 82 and 83 are secured to the endoscope tube 81, for example, by bonding. The manipulator tubes 82 and 83 each include a distal end portion 84 formed of a resin member, and a flexible tube portion 85 made of resin or rubber.

A distal end portion of the tube portion 85 is integrally secured to the distal end portion 84, for example, by bonding. An inner surface of the distal end portion 84 is configured as a tapered hole 86 that serves as both a manipulator protrusion amount determination portion and a joint driving direction determination portion. The tapered hole 86 is configured as an irregularly shaped portion in the present embodiment for determining axial directions of the joints 46, 47, 48 and 49.

The irregularly shaped portion has a shape that uniquely sets the direction of the driving portion 40 provided on the distal end side of the insertion portion distal end piece 4e of the manipulator insertion portion 4i when the insertion portion distal end piece 4e is placed in the tapered hole 86. Specifically, a sectional shape of the tapered hole 86 is, for example, a D shape (see broken lines in FIG. 15) with cord and arc, a pentagon or a hexagon with at least one side having a different length respectively.

The insertion portion distal end piece 4e that constitutes the manipulator insertion portion 4i also has a tapered shape and has a sectional shape of, for example, a D shape, a pentagon or a hexagon with at least one side having a different length respectively like the tapered hole 86. Specifically, as shown in FIG. 17, the insertion portion distal end piece 4e has a D-shaped section and is tapered.

With the configuration, the insertion portion distal end piece 4e is passed through the tapered hole 86 and an inclined surface 4s of the insertion portion distal end piece 4e abuts against an inner surface of the tapered hole 86 to determine a protrusion amount of each of the grasping tool 4A and the electric knife 4B from the distal end surface 82a and a joint driving direction.

The endoscope tube 81 is placed, for example, with reference to a triangular mark 87 in FIG. 14 provided in the distal end portion 24 that constitutes the endoscope insertion portion 21. In the present embodiment, the mark 87 notifies a user of a distance from the distal end surface 2a and placement positions of the manipulator tubes 82 and 83.

Other configurations and operation and effect are the same as in the above described embodiment.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An overtube comprising:
    an endoscope insertion portion passing hole, through which an endoscope insertion portion of an endoscope including an observation optical system in a distal end portion of the endoscope insertion portion is passed, the observation optical system being provided with an image pickup device which has horizontal transfer directions corresponding to lateral observation directions of the observation optical system, and vertical transfer directions corresponding to vertical observation directions of the observation optical system, the endoscope insertion portion passing hole having an endoscope protrusion amount determination portion, and an observation optical system observation direction determination portion, wherein the endoscope protrusion amount determination portion determines a length of the distal end portion of the endoscope insertion portion protruding from a distal end surface of the overtube, and the observation optical system observation direction determination portion determines the vertical transfer directions of the image pickup device which is provided in the endoscope insertion portion inserted through the endoscope insertion portion passing hole to be the vertical observation directions of the observation optical system, and the horizontal transfer directions of the image pickup device to be the lateral observation directions of the observation optical system; and the overtube further comprising a pair of manipulator passing holes, through which manipulator insertion portions of manipulator apparatuses are passed, the manipulator apparatuses each including a driving portion with a plurality of joint pieces connected on a distal end side of the manipulator insertion portion, adjacent joint pieces among the plurality of joint pieces being connected by connecting shafts, and configured as a first joint rotating clockwise and counterclockwise around a first shaft and a second joint rotating clockwise and counterclockwise around a second shaft perpendicular to the first shaft, at least one first joint and at least one second joint being provided in order from the distal end side, the pair of manipulator passing holes each having a central axis parallel to a central axis of the endoscope insertion portion passing hole, and located outside a first phantom line which is tangent to the endoscope insertion portion passing hole and parallel to the vertical transfer directions, or a second phantom line which faces the first phantom line and tangent to the endoscope insertion portion passing hole, the pair of manipulator passing holes each having a manipulator protrusion amount determination portion, and a joint driving direction determination portion, wherein the manipulator protrusion amount determination portion determines a protrusion amount from the distal end surface of the overtube so that the first joint of the driving portion provided in the manipulator insertion portion is placed within an observation range of the observation optical system, and the joint driving direction determination portion maintains the first shaft of the first joint of the driving portion provided in the manipulator insertion portion to be parallel to the vertical transfer directions, and maintains the second shaft of the second joint to be parallel to the horizontal transfer directions;

wherein the endoscope protrusion amount determination portion of the overtube includes:

an abutment surface provided on a side of the endoscope insertion portion passing hole; and an abutment portion provided on the endoscope insertion portion.

2. The overtube according to claim 1, wherein a horizontal transfer direction of a solid-state image pickup device included in the observation optical system of the endoscope corresponds to a lateral observation direction of the observation optical system, a vertical transfer direction corresponds to a vertical observation direction of the observation optical system, and the observation optical system observation direction determination portion of the overtube maintains the first shaft in parallel with the vertical transfer direction, and maintains the second shaft in parallel with the horizontal transfer direction.

3. An overtube comprising:

an endoscope insertion portion passing hole, through which an endoscope insertion portion of an endoscope including an observation optical system in a distal end portion of the endoscope insertion portion is passed, the observation optical system being provided with an image pickup device which has horizontal transfer directions corresponding to lateral observation directions of the observation optical system, and vertical transfer directions corresponding to vertical observation directions of the observation optical system, the endoscope insertion portion passing hole having an endoscope protrusion amount determination portion, and an observation optical system observation direction determination portion, wherein the endoscope protrusion amount determination portion determines a length of the distal end portion of the endoscope insertion portion protruding from a distal end surface of the overtube, and the observation optical system observation direction determination portion determines the vertical transfer directions of the image pickup device which is provided in the endoscope insertion portion inserted through the endoscope insertion portion passing hole to be the vertical observation directions of the observation optical system, and the horizontal transfer directions of the image pickup device to be the lateral observation directions of the observation optical system; and the overtube further comprising a pair of manipulator passing holes, through which manipulator insertion portions of manipulator apparatuses are passed, the manipulator apparatuses each including a driving portion with a plurality of joint pieces connected on a distal end side of the manipulator insertion portion, adjacent joint pieces among the plurality of joint pieces being connected by connecting shafts, and configured as a first joint rotating clockwise and counterclockwise around a first shaft and a second joint rotating clockwise and counterclockwise around a second shaft perpendicular to the first shaft, at least one first joint and at least one second joint being provided in order from the distal end side, the pair of manipulator passing holes each having a central axis parallel to a central axis of the endoscope insertion portion passing hole, and located outside a first phantom line which is tangent to the endoscope insertion portion passing hole and parallel to the vertical transfer directions, or a second phantom line which faces the first phantom line and tangent to the endoscope insertion portion passing hole, the pair of manipulator passing holes each having a manipulator protrusion amount determination portion, and a joint driving direction determination portion, wherein the manipulator protrusion amount determination portion determines a protrusion amount from the distal end surface of the overtube so that the first joint of the driving portion provided in the manipulator insertion portion is placed within an observation range of the observation optical system, and the joint driving direction determination portion maintains the first shaft of the first joint of the driving portion provided in the manipulator insertion portion to be parallel to the vertical transfer directions, and maintains the second shaft of the second joint to be parallel to the horizontal transfer directions;

wherein the observation optical system observation direction determination portion of the overtube also serves as a rotation prevention mechanism for preventing axial rotation of the endoscope insertion portion in the endoscope insertion portion passing hole.

4. An overtube comprising:

an endoscope insertion portion passing hole, through which an endoscope insertion portion of an endoscope including an observation optical system in a distal end portion of the endoscope insertion portion is passed, the observation optical system being provided with an image pickup device which has horizontal transfer directions corresponding to lateral observation directions of the observation optical system, and vertical transfer directions corresponding to vertical observation directions of the observation optical system, the endoscope insertion portion passing hole having an endoscope protrusion amount determination portion, and an observation optical system observation direction determination portion, wherein the endoscope protrusion amount determination portion determines a length of the distal end portion of the endoscope insertion portion protruding from a distal end surface of the overtube, and the observation optical system observation direction determination portion determines the vertical transfer directions of the image pickup device which is provided in the endoscope insertion portion inserted through the endoscope insertion portion passing hole to be the vertical observation directions of the observation optical system, and the horizontal transfer directions of the image pickup device to be the lateral observation directions of the observation optical system; and the overtube further comprising a pair of manipulator passing holes, through which manipulator insertion portions of manipulator apparatuses are passed, the manipulator apparatuses each including a driving portion with a plurality of joint pieces connected on a distal end side of the manipulator insertion portion, adjacent joint pieces among the plurality of joint pieces being connected by connecting shafts, and configured as a first joint rotating clockwise and counterclockwise around a first shaft and a second joint rotating clockwise and counterclockwise around a second shaft perpendicular to the first shaft, at least one first joint and at least one second joint being provided in order from the distal end side, the pair of manipulator passing holes each having a central axis parallel to a central axis of the endoscope insertion portion passing hole, and located outside a first phantom line which is tangent to the endoscope insertion portion passing hole and parallel to the vertical transfer directions, or a second phantom line which faces the first phantom line and tangent to the endoscope insertion portion passing hole, the pair of manipulator passing holes each having a manipulator protrusion amount determination portion, and a joint driving direction determination portion, wherein the manipulator protrusion amount determination portion determines a protrusion amount from the distal end surface of the overtube so that the first joint of the driving portion provided in the manipulator insertion portion is placed within an observation range of the observation optical system, and the joint driving direction determination portion maintains the first shaft of the first joint of the driving portion provided in the manipulator insertion portion to be parallel to the vertical transfer directions, and maintains the second shaft of the second joint to be parallel to the horizontal transfer directions;

wherein the manipulator protrusion amount determination portion of the overtube includes:

an abutment surface provided on a side of the manipulator passing hole; and an abutment portion provided on the manipulator insertion portion.

5. An overtube comprising:

an endoscope insertion portion passing hole, through which an endoscope insertion portion of an endoscope including an observation optical system in a distal end portion of the endoscope insertion portion is passed, the observation optical system being provided with an image pickup device which has horizontal transfer directions corresponding to lateral observation directions of the observation optical system, and vertical transfer directions corresponding to vertical observation directions of the observation optical system, the endoscope insertion portion passing hole having an endoscope protrusion amount determination portion, and an observation optical system observation direction determination portion, wherein the endoscope protrusion amount determination portion determines a length of the distal end portion of the endoscope insertion portion protruding from a distal end surface of the overtube, and the observation optical system observation direction determination portion determines the vertical transfer directions of the image pickup device which is provided in the endoscope insertion portion inserted through the endoscope insertion portion passing hole to be the vertical observation directions of the observation optical system, and the horizontal transfer directions of the image pickup device to be the lateral observation directions of the observation optical system; and the overtube further comprising a pair of manipulator passing holes, through which manipulator insertion portions of manipulator apparatuses are passed, the manipulator apparatuses each including a driving portion with a plurality of joint pieces connected on a distal end side of the manipulator insertion portion, adjacent joint pieces among the plurality of joint pieces being connected by connecting shafts, and configured as a first joint rotating clockwise and counterclockwise around a first shaft and a second joint rotating clockwise and counterclockwise around a second shaft perpendicular to the first shaft, at least one first joint and at least one second joint being provided in order from the distal end side, the pair of manipulator passing holes each having a central axis parallel to a central axis of the endoscope insertion portion passing hole, and located outside a first phantom line which is tangent to the endoscope insertion portion passing hole and parallel to the vertical transfer directions, or a second phantom line which faces the first phantom line and tangent to the endoscope insertion portion passing hole, the pair of manipulator passing holes each having a manipulator protrusion amount determination portion, and a joint driving direction determination portion, wherein the manipulator protrusion amount determination portion determines a protrusion amount from the distal end surface of the overtube so that the first joint of the driving portion provided in the manipulator insertion portion is placed within an observation range of the observation optical system, and the joint driving direction determination portion maintains the first shaft of the first joint of the driving portion provided in the manipulator insertion portion to be parallel to the vertical transfer directions, and maintains the second shaft of the second joint to be parallel to the horizontal transfer directions;

wherein the joint driving direction determination portion of the overtube also serves as a rotation prevention mechanism for preventing axial rotation of the manipulator insertion portion in the manipulator passing hole.

6. The overtube according to claim 1, wherein the overtube is a multi-lumen tube at least including a through hole that constitutes the endoscope insertion portion passing hole and two through holes that constitute the manipulator passing hole.

7. The overtube according to claim 1, wherein the overtube includes:
a first tube body including the endoscope insertion portion passing hole; and
two second tube bodies including the manipulator passing holes.

8. An endoscope system comprising:
an endoscope;
a manipulator apparatus; and
an overtube,
wherein the endoscope includes an observation optical system in a distal end portion of an endoscope insertion portion, the observation optical system being provided with an image pickup device which has horizontal transfer directions corresponding to lateral observation directions of the observation optical system, and vertical transfer directions corresponding to vertical observation directions of the observation optical system,
the manipulator apparatus includes a driving portion with a plurality of joint pieces connected on a distal end side of a manipulator insertion portion,
adjacent joint pieces among the plurality of joint pieces are connected by connecting shafts, and configured as a first joint rotating clockwise and counterclockwise around a first shaft and a second joint rotating clockwise and counterclockwise around a second shaft perpendicular to the first shaft, at least one first joint and at least one second joint are provided in order from the distal end side,
the overtube includes an endoscope insertion portion passing hole through which the endoscope insertion portion of the endoscope is passed, and a pair of manipulator passing holes through which the manipulator insertion portions of the manipulator apparatuses are passed, the pair of manipulator passing holes each having a central axis parallel to a central axis of the endoscope insertion portion passing hole, and located outside a first phantom line which is tangent to the endoscope insertion portion passing hole and parallel to the vertical transfer directions, or a phantom line which faces the first phantom line and tangent to the endoscope insertion portion passing hole, the endoscope insertion portion passing hole includes an endoscope protrusion amount determination portion and an observation optical system observation direction determination portion, the manipulator passing hole includes a manipulator protrusion amount determination portion and a joint driving direction determination portion, the endoscope protrusion amount determination portion determines a length of a distal end portion of the endoscope insertion portion protruding from a distal end surface of the overtube, the observation optical system observation direction determination portion determines the vertical observation directions of the image pickup device which is provided in the endoscope insertion portion inserted through the endoscope insertion portion passing hole to be vertical observation directions of the observation optical system, and determines the horizontal transfer directions of the image pickup device to be the lateral observation directions of the observation optical system, the manipulator protrusion amount determination portion determines a protrusion amount from the distal end surface of the overtube so that the first joint of the driving portion provided in the manipulator insertion portion is placed within an observation range of the observation optical system, and the joint driving direction determination portion maintains the first shaft of the first joint of the driving portion provided in the manipulator insertion portion to be parallel to the vertical transfer directions, and maintains the second shaft of the second joint to be parallel to the horizontal transfer directions;

wherein the endoscope protrusion amount determination portion includes:
an abutment surface provided on a side of the endoscope insertion portion passing hole; and
an abutment portion provided on the endoscope insertion portion.

9. The endoscope system according to claim 8, wherein a horizontal transfer direction of a solid-state image pickup device included in the observation optical system of the endoscope corresponds to a lateral observation direction of the observation optical system, a vertical transfer direction corresponds to a vertical observation direction of the observation optical system,
the first shaft is maintained in parallel with the vertical transfer direction by the observation optical system observation direction determination portion, and the second shaft is maintained in parallel with the horizontal transfer direction by the observation optical system observation direction determination portion.

10. An endoscope system comprising:
an endoscope;
a manipulator apparatus; and
an overtube,
wherein the endoscope includes an observation optical system in a distal end portion of an endoscope insertion portion, the observation optical system being provided with an image pickup device which has horizontal transfer directions corresponding to lateral observation directions of the observation optical system, and vertical transfer directions corresponding to vertical observation directions of the observation optical system, the manipulator apparatus includes a driving portion with a plurality of joint pieces connected on a distal end side of a manipulator insertion portion, adjacent joint pieces among the plurality of joint pieces are connected by connecting shafts, and configured as a first joint rotating clockwise and counterclockwise around a first shaft and a second joint rotating clockwise and counterclockwise around a second shaft perpendicular to the first shaft, at least one first joint and at least one second joint are provided in order from the distal end side, the overtube includes an endoscope insertion portion passing hole through which the endoscope insertion portion of the endoscope is passed, and a pair of manipulator passing holes through which the manipulator insertion portions of the manipulator apparatuses are passed, the pair of manipulator passing holes each having a central axis parallel to a central axis of the endoscope insertion portion passing hole, and located outside a first phantom line which is tangent to the endoscope insertion portion passing hole and parallel to the vertical transfer directions, or a phantom line which faces the first phantom line and tangent to the endoscope insertion portion passing hole, the endoscope insertion portion passing hole includes an endoscope protrusion amount determination portion and an observation optical system observation direction determination portion, the manipulator passing hole includes a manipulator protrusion amount determination portion and a joint driving direction determination portion, the endoscope protrusion amount determination portion determines a length of a distal end portion of the endoscope insertion portion protruding from a distal end surface of the overtube, the observation optical system observation direction determination portion determines the vertical observation directions of the image pickup device which is provided in the endoscope insertion portion inserted through the endoscope insertion portion passing hole to be vertical observation directions of the observation optical system, and determines the horizontal transfer directions of the image pickup device to be the lateral observation directions of the observation optical system, the manipulator protrusion amount determination portion determines a protrusion amount from the distal end surface of the overtube so that the first joint of the driving portion provided in the manipulator insertion portion is placed within an observation range of the observation optical system, and the joint driving direction determination portion maintains the first shaft of the first joint of the driving portion provided in the manipulator insertion portion to be parallel to the vertical transfer directions, and maintains the second shaft of the second joint to be parallel to the horizontal transfer directions;

wherein the observation optical system observation direction determination portion also serves as a rotation prevention mechanism for preventing axial rotation of the endoscope insertion portion in the endoscope insertion portion passing hole.

11. An endoscope system comprising:
an endoscope;
a manipulator apparatus; and
an overtube,
wherein the endoscope includes an observation optical system in a distal end portion of an endoscope insertion portion, the observation optical system being provided with an image pickup device which has horizontal transfer directions corresponding to lateral observation directions of the observation optical system, and vertical transfer directions corresponding to vertical observation directions of the observation optical system, the manipulator apparatus includes a driving portion with a plurality of joint pieces connected on a distal end side of a manipulator insertion portion, adjacent joint pieces among the plurality of joint pieces are connected by connecting shafts, and configured as a first joint rotating clockwise and counterclockwise around a first shaft and a second joint rotating clockwise and counterclockwise around a second shaft perpendicular to the first shaft, at least one first joint and at least one second joint are provided in order from the distal end side, the overtube includes an endoscope insertion portion passing hole through which the endoscope insertion portion of the endoscope is passed, and a pair of manipulator passing holes through which the manipulator insertion portions of the manipulator apparatuses are passed, the pair of manipulator passing holes each having a central axis parallel to a central axis of the endoscope insertion portion passing hole, and located outside a first phantom line which is tangent to the endoscope insertion portion passing hole and parallel to the vertical transfer directions, or a phantom line which faces the first phantom line and tangent to the endoscope insertion portion passing hole, the endoscope insertion portion passing hole includes an endoscope protrusion amount determination portion and an observation optical system observation direction determination portion, the manipulator passing hole includes a manipulator protrusion amount determination portion and a joint driving direction determination portion, the endoscope protrusion amount determination portion determines a length of a distal end portion of the endoscope insertion portion protruding from a distal end surface of the overtube, the observation optical system observation direction determination portion determines the vertical observation directions of the image pickup device which is provided in the endoscope insertion portion inserted through the endoscope insertion portion passing hole to be vertical observation directions of the observation optical system, and determines the horizontal transfer directions of the image pickup device to be the lateral observation directions of the observation optical system, the manipulator protrusion amount determination portion determines a protrusion amount from the distal end surface of the overtube so that the first joint of the driving portion provided in the manipulator insertion portion is placed within an observation range of the observation optical system, and the joint driving direction determination portion maintains the first shaft of the first joint of the driving portion provided in the manipulator insertion portion to be parallel to the vertical transfer directions, and maintains the second shaft of the second joint to be parallel to the horizontal transfer directions;

wherein the manipulator protrusion amount determination portion includes:
an abutment surface provided on a side of the manipulator passing hole; and an abutment portion provided on the manipulator insertion portion.

12. An endoscope system comprising:
an endoscope;
a manipulator apparatus; and
an overtube,
wherein the endoscope includes an observation optical system in a distal end portion of an endoscope insertion portion, the observation optical system being provided with an image pickup device which has horizontal transfer directions corresponding to lateral observation directions of the observation optical system, and vertical transfer directions corresponding to vertical observation directions of the observation optical system,
the manipulator apparatus includes a driving portion with a plurality of joint pieces connected on a distal end side of a manipulator insertion portion,
adjacent joint pieces among the plurality of joint pieces are connected by connecting shafts, and configured as a first joint rotating clockwise and counterclockwise around a first shaft and a second joint rotating clockwise and counterclockwise around a second shaft perpendicular to the first shaft, at least one first joint and at least one second joint are provided in order from the distal end side,
the overtube includes an endoscope insertion portion passing hole through which the endoscope insertion portion of the endoscope is passed, and a pair of manipulator passing holes through which the manipulator insertion portions of the manipulator apparatuses are passed, the pair of manipulator passing holes each having a central axis parallel to a central axis of the endoscope insertion portion passing hole, and located outside a first phantom line which is tangent to the endoscope insertion portion passing hole and parallel to the vertical transfer directions, or a phantom line which faces the first phantom line and tangent to the endoscope insertion portion passing hole,
the endoscope insertion portion passing hole includes an endoscope protrusion amount determination portion and an observation optical system observation direction determination portion, the manipulator passing hole includes a manipulator protrusion amount determination portion and a joint driving direction determination portion,
the endoscope protrusion amount determination portion determines a length of a distal end portion of the endoscope insertion portion protruding from a distal end surface of the overtube,
the observation optical system observation direction determination portion determines the vertical observation directions of the image pickup device which is provided in the endoscope insertion portion inserted through the endoscope insertion portion passing hole to be vertical observation directions of the observation optical system, and determines the horizontal transfer directions of the image pickup device to be the lateral observation directions of the observation optical system,
the manipulator protrusion amount determination portion determines a protrusion amount from the distal end surface of the overtube so that the first joint of the driving portion provided in the manipulator insertion portion is placed within an observation range of the observation optical system, and
the joint driving direction determination portion maintains the first shaft of the first joint of the driving portion provided in the manipulator insertion portion to be parallel to the vertical transfer directions, and maintains the second shaft of the second joint to be parallel to the horizontal transfer directions;
wherein the joint driving direction determination portion also serves as a rotation prevention mechanism for preventing axial rotation of the manipulator insertion portion in the manipulator passing hole.

13. The endoscope system according to claim 8, wherein the overtube is a multi-lumen tube at least including a through hole that constitutes the endoscope insertion portion passing hole and two through holes that constitute the manipulator passing hole.

14. The endoscope system according to claim 8, wherein the overtube includes:
a first tube body including the endoscope insertion portion passing hole; and
two second tube bodies including the manipulator passing holes.

* * * * *